US006258807B1

(12) United States Patent
Helton et al.

(10) Patent No.: US 6,258,807 B1
(45) Date of Patent: *Jul. 10, 2001

(54) METHOD FOR TREATING PAIN

(75) Inventors: David R. Helton, Springfield, VA (US); Harlan E. Shannon, Carmel, IN (US); Daniel E. Womer, Thornton, CO (US); Mary J. Kallman, Greenfield, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/823,460

(22) Filed: Mar. 24, 1997

Related U.S. Application Data

(60) Provisional application No. 60/014,131, filed on Mar. 25, 1996, provisional application No. 60/014,153, filed on Mar. 25, 1996, and provisional application No. 60/014,133, filed on Mar. 25, 1996.

(51) Int. Cl.⁷ ..................................................... A61K 31/54
(52) U.S. Cl. ............................................. 514/220; 514/315
(58) Field of Search ...................................... 514/315, 220

(56) References Cited

U.S. PATENT DOCUMENTS

| 4,216,149 | * | 8/1980 | Hofmann et al. ................. 260/243.3 |
| 5,229,382 | * | 7/1993 | Chakrabarti et al. ................. 514/220 |
| 5,457,101 | | 10/1995 | Greenwood et al. . |
| 5,605,911 | * | 2/1997 | Olney et al. ......................... 514/315 |
| 5,703,232 | * | 12/1997 | Bunnell et al. ..................... 540/557 |
| 5,945,416 | * | 8/1999 | Shannon et al. ..................... 514/220 |

* cited by examiner

Primary Examiner—Keith D. MacMillan
Assistant Examiner—Thomas Prasthofer
(74) Attorney, Agent, or Firm—Arleen Palmberg; Macharri Vorndran-Jones; Nancy Harrison

(57) ABSTRACT

The present invention provides a method for treating pain comprising administering an analgesic dosage of olanzapine to an animal in need of such treatment.

17 Claims, No Drawings

METHOD FOR TREATING PAIN

This application claims the benefit of U.S. Provisional Application No. 60/014,131, filed Mar. 25, 1996, U.S. Provisional Application No. 60/014,153, filed Mar. 25, 1996, and U.S. Provisional Application No. 60/014,133, filed Mar. 25, 1996.

FIELD OF THE INVENTION

This invention provides a method for using 2-methyl-4-(4-methyl-1-piperazinyl)-10H-thieno[2,3-b][1,5] benzodiazepine, (hereinafter referred as "olanzapine") for the treatment of pain. The present invention provides a method which is especially useful for the treatment of acute pain, nociceptive, and neuropathic pain.

BACKGROUND OF THE INVENTION

The present invention provides a method for treating pain.

The present invention provides a method for treating acute self-limiting ailments, low-grade somatic-type acute pain, including for example, but not limited to headache, arthritis, simple muscle strain, and dysmenorrhea. The invention further provides a method for treating neuropathic pain. Additionally, this invention provides a method for treating nociceptive pain.

There is a demand for more active analgesic agents with diminished side effects and toxicity and which are non-addictive. The ideal analgesic would reduce the awareness of pain, produce analgesia over a wide range of pain types, act satisfactorily whether given orally or parenterally, produce minimal or no side effects, be free from tendency to produce tolerance and drug dependence.

Applicants have discovered that olanzapine can provide many of the characteristics of an ideal analgesic for the treatment of pain.

It is known that olanzapine can provide antipsychotic activity and is commercially available for the treatment of psychosis. Olanzapine is a known compound and described in U.S. Pat. No. 5,229,382 as being useful for the treatment of schizophrenia, schizophreniform disorder, acute mania, mild anxiety states, and psychosis. U.S. Pat. No. 5,229,382 is herein incorporated by reference in its entirety. Surprisingly, and in accordance with this invention, Applicants have discovered that olanzapine can be useful for the treatment of pain. Olanzapine could address a long felt need for a safe and effective treatment for acute pain.

SUMMARY OF THE INVENTION

The present invention provides a method for treating pain comprising administering an effective amount of olanzapine to an animal in need of such treatment.

The present invention provides a method for treating acute pain comprising administering to a patient in need thereof, an analgesic dosage of olanzapine or a pharmaceutically acceptable salt thereof.

It is preferred that the acute pain shall be selected from the group consisting of headache, arthritis, simple muscle strain, and dysmenorrhea.

The present invention provides a method for treating nociceptive pain comprising administering to a patient in need thereof, an analgesic dosage of olanzapine or a pharmaceutically acceptable salt thereof.

The present invention provides a method for treating neuropathic pain comprising administering to a patient in need thereof, an analgesic dosage of olanzapine or a pharmaceutically acceptable salt thereof.

It is preferred that the neuropathic pain is selected from the group consisting of chronic lower back pain, pain associated with arthritis, cancer-associated pain, herpes neuralgia, phantom limb pain, central pain, opioid resistant neuropathic pain, bone injury pain, and pain during labor and delivery.

It is preferred that the nociceptive pain is selected from the group consisting of post-operative pain, cluster headaches, dental pain, surgical pain, pain resulting from severe, for example third degree, burns, post partum pain, angina pain, genitourinary tract related pain, and including cystitis.

Finally, the present invention can provide a method for treating inflammation in an animal comprising administering an anti-inflammatory dose of olanzapine to an animal in need of such treatment.

DETAILED DESCRIPTION OF THE INVENTION

Olanzapine is of the formula

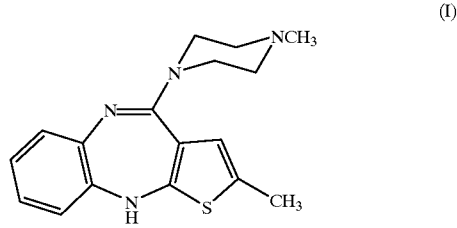

(I)

or an acid addition salt thereof.

It is especially preferred that olanzapine will be the Form II olanzapine polymorph having a typical x-ray powder diffraction pattern as represented by the following interplanar spacings:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007 |

A typical example of an x-ray diffraction pattern for Form II is as follows wherein d represents the interplanar spacing and $I/I_1$ represents the typical relative intensities:

| d | I/I$_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

The x-ray diffraction patterns set out herein were obtained using a Siemens D5000 x-ray powder diffractometer having a copper K$_\alpha$ radiation source of wavelength, 1=1.541 Å.

It is further preferred that the Form II olanzapine polymorph will be administered as the substantially pure Form II olanzapine polymorph.

As used herein "substantially pure" refers to Form II associated with less than about 5% Form I, preferably less than about 2% Form I, and more preferably less than about 1% Form I. Further, "substantially pure" Form II should contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the polymorph of the invention should contain less than 0.5% of associated water.

The polymorph obtainable by the process taught in the '382 patent will be designated as Form I and has a typical x-ray powder diffraction pattern substantially as follows, obtained using a Siemens D5000 x-ray powder diffractometer, wherein d represents the interplanar spacing:

| d |
|---|
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956 |

A typical example of an x-ray diffraction pattern for Form I is as follows wherein d represents the interplanar spacing and I/I$_1$ represents the typical relative intensities:

| d | I/I$_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns herein were obtained with a copper K$_\alpha$ of wavelength 1=1.541 Å. The interplanar spacings in the column marked "d" are in Angstroms. The typical relative intensities are in the column marked "I/I$_1$".

As used herein, "animal" refers to a vertebrate animal. The most preferred animal is a mammal. As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

Olanzapine is effective over a wide dosage range; however, it is desirable to administer a dosage that is as low as possible. For example, dosages per day of the olanzapine will normally fall within the range of about 0.1 mg to about 30 mg per day. However, it will be understood that the amount of the compound actually administered will be determined by a physician, in the light of the relevant circumstances including the type of acute pain to be treated, the age, weight, and response of the individual patient, the severity of the patient's symptoms, and the chosen route of administration, and therefore the above dosage ranges are not intended to limit the scope of the invention in any way. While the present compounds are preferably administered orally to humans susceptible to or suffering from pain, the compounds may also be administered by a variety of other routes such as the transdermal, parenteral, subcutaneous, intranasal, intramuscular and intravenous routes. Such formulations may be designed to provide delayed or controlled release using formulation techniques which are known in the art.

As used herein the term "treating" includes prophylaxis of pain in a patient having a tendency to develop such pain, and the amelioration or elimination of the developed pain once it has been established or alleviation of the characteristic symptoms of such pain. This invention envisions that the treatment of pain is most preferably the treatment of pain selected from the group consisting of acute pain, nociceptive pain, and neuropathic pain.

As used herein the term "acute pain" shall refer acute self-limiting ailments and low-grade somatic type acute pain. For example, the term includes, but is not limited to headache, arthritis, simple muscle strains, and dysmenorrhea.

As used herein the term "nociceptive pain" shall refer to pain that is transmitted across intact neuronal pathways.

As used herein the term "neuropathic pain" shall refer to pain caused by damage to neural structures, often involving neural supersensitivity.

It is preferred that the neuropathic pain is selected from the group consisting of chronic lower back pain, pain associated with arthritis, cancer-associated pain, herpes neuralgia, phantom limb pain, central pain, opioid resistant neuropathic pain, bone injury pain, and pain during labor and delivery.

It is preferred that the nociceptive pain is selected from the group consisting of post-operative pain, cluster headaches, dental pain, surgical pain, pain resulting from severe, for example third degree, burns, post partum pain, angina pain, genitourinary tract related pain, and including cystitis.

The results of pharmacological studies show that olanzapine has muscarinic cholinergic receptor activity. The compound is active at the dopamine D-1 and D-2 receptors as indicated by an IC50 of less than 1 $\mu$M in the 3H-SCH233390 (Billard, et al. Life Sciences 35:1885 (1984)) and the 3H spiperone (Seeman et al Nature 216:717 (1976)) binding assays respectively. Further, olanzapine is active at the 5-HT-2 receptor and 5-HT1C receptor. The complex pharmacological profile of the compound provides a medicament which can be useful for the treatment of pain.

The dosage administered will, of course, vary depending on known factors such as the pharmacodynamic characteristics of the particular agent, and its mode and route of administration; age, health, and weight of the recipient; nature and extent of the symptoms, kind of concurrent treatment, frequency of treatment, and the effect desired. Usually, the daily dosage can be such that the active ingredient is administered at a daily dosage of from about 1 mg to about 30 mg olanzapine.

Compositions suitable for internal administration contain from about one half (0.5) milligrams to about 100 milligrams of active ingredient per unit. In these pharmaceutical compositions, the active ingredient will ordinarily be present in an amount of from about 0.5% to about 95% by weight based on the total weight of the composition.

Typical compositions include olanzapine or a pharmaceutically acceptable acid addition salt thereof associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, olanzapine is dispensed in unit form comprising from about 0.1 mg to about 30 mg in a pharmaceutically acceptable carrier per unit dosage.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

The compositions of this invention may be suitable for administration to an animal. Such animals include both domestic animals, for example livestock, laboratory animals, and household pets, and non-domestic animals such as wildlife. More preferredly, the animal is a vertebrate. Most preferredly, a compound of this invention shall be administered to a mammal. It is especially preferred that the animal is a domestic mammal or a human. The most preferred mammal is a human. For such purposes, a compound of this invention may be administered as a feed additive.

Utility Test Methods

The unexpected analgesic activity of olanzapine is evidenced by tests intially conducted on mice. Mice weighing from about 18–22 grams at the time of testing are used for the following studies. All mice are dosed by the oral route with olanzapine. Doses are coded using a code unknown to the observer.

Mouse Writhing Test

An accepted standard for detecting an comparing the analgesic activity of different classes of analgesic compounds for which there is a good correlation with human analgesic activity is the prevention of acetic acid-induced writhing in mice.

Adult, male CD-1 [Crl:CDR-1(ICR)] mice (approximately 4–5 weeks of age), were obtained from Charles River Laboratories, Portage, Mich., and acclimated at least 3 days before testing. Only healthy mice weighing between 22 and 35 g were included in testing. Mice were housed 10/cage in plastic gang cages and given Certified Rodent Chow and water ad libitum. Bedding was changed twice weekly. Room temperature was maintained at 22 +/−4° C. and relative humidity was maintained between 30% and 70%. The photoperiod was 12 hours of light and 12 hours of dark, with dark onset at approximately 1800 hours.

Throughout the study, suspensions were prepared at target concentrations of 0, 0.3, 0.1, 0.3, and 1 mg olanzapine/ml by the addition of 10% acacia in purified water. The vehicle control consisted of 10% acacia in purified water.

Analgesic activity following administration of olanzapine was evaluated using acetic acid-induced writhing. An intraperitoneal injection of acetic acid in mice causes them to exhibit contractions of the abdominal muscles, or writhe (Siegmund et al., 1957). Administration of either opioid or nonopioid analgesics reduces the amount of writing (Collier, 1964). Writhing has been used to define the pharmacology of analgesics such as aspirin and morphine. Approximately 60 minutes following oral administration of olanzapine (0, 0.3, 1, 3, or 10 mg/kg), each mouse received 0.5% acetic acid (0.01 ml/g, intraperitoneal). Mice were placed in individual clear observation chambers and the total number of writhes made by each mouse was counted between 5 and 10 minutes following administration of acetic acid. See, Haubrich, D. R., Ward, S. J., Baizman, E., Bell, M. R., Bradford, J., Ferrari, R., Miller, M., Perrone, M., Pierson, A. K., Saelens, J. K. and Luttinger, D.: "Pharmacology of pravadoline: a new analgesic agent", *The Journal of Pharmacology and Experimental Therapeutics* 255 (1990) 511–522.

Surprisingly, such experiments demonstrate that olanzapine provides a significant analgesic effect at doses of 1, 3, and 10 mg/kg when compared to controls.

Another accepted standard for detecting and comparing the analgesic activity of different classes of analgesic compounds for which there is a good correlation with human analgesic activity is the prevention of phenyl-p-benzoquinone induced writhing in mice. [H. Blumberg et al. Proc. Soc. Exp. biol. Med., 118, 763–766 (1965)].

Mice, treated with various doses of olanzapine or vehicle are injected intraperitoneally with a standard challenge dose of phenyl-p-benzoquinone 5 minutes prior to a designated observation period. The pheyl-p-benzoquinone is prepared as about 0.1 mg/ml solution in about 5% by volume of ethanol in water. The writhing dose is 1.25 mg/kg injected at a volume of about 0.25 ml/10 g. For scoring purposes a "writhe" is indicated by whole body stretching or contracting of the abdomen during an observation period beginning about five minutes after the phenyl-p-benzoquinone dose.

All ED50 values and their 95% confidence limits are determined using accepted numerical methods. For example, see W. F. Thompson, *Bacteriological Rev.*, 11, 115–145 (1947).

Tail Flick Test.

Tail-flick has been used to define or monitor analgesic levels following exposure to a variety of compounds (D'Amour and Smith, 1941; Harris and Pierson, 1964). The apparatus can be used to test mice, rats or monkeys by focusing a beam of light on the tail and evaluating latency to tail-flick. This test has proven useful for screening weak or strong analgesics (Dewey et. al., 1969).

Tail flick was used to evaluate the analgesic effects of olanzapine. Approximately 60 minutes following oral administration of olanzapine (0, 0.3, 1, 3, or 10 mg/kg) mice were placed in a holding tube and the time required for each mouse to react (tail flick) to the heat from a beam of light focused on the tail was recorded (Tail Flick Apparatus, Columbus Instruments, Columbus, Ohio).

Olanzapine produced significant analgesic activity with significant increases in tail flick latencies at 1, 3, and 10 mg/kg with respect to control latencies.

The unexpected neuropathic analgesic activity of olanzapine is evidenced by the Sciatic nerve ligation model as follows:

Sciatic Nerve Ligation Model:

Rats are anesthetized and a nerve ligation procedure performed. The common sciatic nerve is exposed and 4 ligatures tied loosely around it with about 1 mm spacing. One day to 10 weeks after surgery, the nociceptive testing is performed. Rats are orally administered various doses of olanzapine or placebo, prior to testing. Responses to noxious heat are determined by placing the rats in a chamber with a clear glass floor and aiming at the plantar surface of the affected foot a radiant heat source from beneath the floor. Increased latency to withdraw the hind paw is demonstrative of analgesic activity. Responses to normally innocuous mechanical stimuli is determined by placing the rats in a chamber with a screen floor and stimulating the plantar surface of the hind paw with graduated von Frey hairs which are calibrated by the grams of force required to bend them. Rats with sciatic nerve ligation respond to lower grams of mechanical stimulation by reflexive withdrawal of the foot than unoperated rats. This response to stimuli which are normally innocuous is termed allodynia. Increases in the grams of mechanical force required to produce foot withdrawal is demonstrative of antiallodynic activity.

Bennett, G. J. and Xie, Y.-K, "A peripheral mononeuropathy in rat that produces disorders of pain sensation like those seen in man", *Pain* 33 (1988) 87–107.

Clinical Observations.

A double-blind multicenter clinical trial is designed to assess the safety and efficacy of olanzapine. Patients are randomized to olanzapine or placebo. Patients are monitored for perception of pain using standard methods.

The materials for the present invention can be purchased or prepared by a variety of procedures well known to those of ordinary skill in the art. Olanzapine can be prepared as described by Chakrabarti in U.S. Pat. No. 5,229,382 ('382), herein incorporated by reference in its entirety. Further, the following preparations illustrate a method for preparing of the especially preferred Form II olanzapine polymorph.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention.

PREPARATION 1

Technical Grade Olanzapine

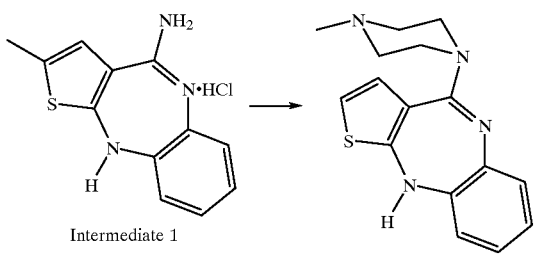

Intermediate 1

In a suitable three neck flask the following was added:
Dimethylsulfoxide (analytical): 6 volumes
Intermediate 1: 75 g
N-Methylpiperazine (reagent): 6 equivalents
Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained at that temperature throughout the duration of the reaction. The reactions were followed by HPLC until $^2$ 5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine. Yield: 76.7%; Potency: 98.1%

PREPARATION 2

Form II Olanzapine Polymorph

A 270 g sample of technical grade 2-methyl-4-(4-methyl-1-piperazinyl)-10H-thieno[2,3-b][1,5]benzodiazepine was suspended in anhydrous ethyl acetate (2.7 L). The mixture was heated to 76° C. and maintained at 76° C. for 30 minutes. The mixture was allowed to cool to 25° C. The resulting product was isolated using vacuum filtration. The product was identified as Form II using x-ray powder analysis. Yield: 197 g.

The process described above for preparing Form II provides a pharmaceutically elegant product having potency ≧97%, total related substances <0.5% and an isolated yield of >73%.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the olanzapine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer. The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating:

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets:

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

We claim:

1. A method for treating neuropathic pain comprising administering an analgesic dosage of olanzapine to a mammal in need of such treatment.

2. A method of claim 1 wherein the analgesic dosage of olanzapine is from about 5 mg to about 30 mg per day.

3. A method of claim 2 wherein the analgesic dosage of olanzapine is from about 5 mg to about 25 mg per day.

4. A method of claim 1 wherein the mammal is a human.

5. A method of claim 4 wherein the neuropathic pain is selected from the group consisting of chronic lower back pain, pain associated with arthritis, cancer-associated pain, herpes neuralgia, phantom limb pain, central pain, opioid resistant neuropathic pain, bone injury pain, and pain during labor and delivery.

6. A method of claim 1 wherein olanzapine is Form II olanzapine polymorph.

7. A method for treating nociceptive pain comprising administering an analgesic dosage of olanzapine to a mammal in need of such treatment.

8. A method of claim 7 wherein the analgesic dosage of olanzapine is from about 5 mg to about 25 mg per day.

9. A method of claim 7 wherein olanzapine is Form II olanzapine polymorph.

10. A method of claim 7 wherein the mammal is a human.

11. A method for treating inflammation comprising administering an anti-inflammatory dose of olanzapine to an animal in need of such treatment.

12. A method of claim 11 wherein the animal is a human.

13. A method for treating a neuropathic pain selected from post-operative pain, a cluster headache, dental pain, surgical pain, pain resulting from a severe burn, post-partum pain, angina pain or genito-urinary-tract-related pain in a human comprising administering an analgesic dosage of olanzapine to the human.

14. A method of claim 13 wherein the pain is a genito-urinary-tract-related pain caused by cystitis.

15. A method for treating an acute pain associated with arthritis, simple muscle strain or dysmenorrhea in a mammal, comprising administering an analgesic dosage of olanzapine to the mammal.

16. A method for treating a headache in a mammal, comprising administering an analgesic dosage of olanzapine to the mammal.

17. A method for treating neuropathic pain associated with arthritis in a human comprising administering an analgesic dosage of olanzapine to the human.

* * * * *